United States Patent [19]

Mattheissen

[11] Patent Number: 4,954,718

[45] Date of Patent: Sep. 4, 1990

[54] CIRCUIT ARRANGEMENT FOR DRIVING A PULSE-MODULATED INFRARED-RADIATION SOURCE

[75] Inventor: Hans Mattheissen, Gross Parin, Fed. Rep. of Germany

[73] Assignee: Drägerwerk Aktiengesellschaft, Lübeck, Fed. Rep. of Germany

[21] Appl. No.: 361,487

[22] Filed: Jun. 5, 1989

[30] Foreign Application Priority Data

Jun. 11, 1988 [DE] Fed. Rep. of Germany ....... 3819987

[51] Int. Cl.$^5$ ............................................. H01K 1/02
[52] U.S. Cl. .............................. 250/493.1; 250/338.1; 250/350; 250/351; 250/504 R
[58] Field of Search ................... 250/493.1, 338.1, 352, 250/350, 351, 504 R

[56] References Cited

U.S. PATENT DOCUMENTS

| | | | |
|---|---|---|---|
| 2,876,361 | 3/1959 | Hutchinson | 250/493.1 |
| 2,931,939 | 4/1960 | Christofilos et al. | 250/493.1 |
| 3,077,539 | 2/1963 | Blau, Jr. et al. | 250/493.1 |
| 3,095,506 | 6/1963 | Dewey et al. | 250/504 R |
| 3,309,881 | 3/1967 | Beerman | 250/493.1 |
| 4,103,174 | 7/1978 | McClatchie et al. | 250/493.1 |
| 4,620,104 | 10/1986 | Nordal et al. | 250/504 R |
| 4,754,141 | 6/1988 | Mindock | 250/504 R |
| 4,803,370 | 2/1989 | Eckles | 250/504 R |

FOREIGN PATENT DOCUMENTS 3043332 7/1982 Fed. Rep. of Germany .

Primary Examiner—Jack I. Berman
Assistant Examiner—Kiet T. Nguyen
Attorney, Agent, or Firm—Walter Ottesen

[57] ABSTRACT

A circuit arrangement for providing a pulse modulated power feed to an infrared radiation source is disclosed. The radiation of the radiation source is detectable by a receiver and the circuit arrangement is improved such that the radiation source is as independent as possible from its radiation characteristics as well as from its thermal characteristics and can deliver a rapid and easily processable measuring signal to the receiver uninfluenced by ambient conditions. For this purpose, the power feed is controllable by means of a control unit during the pulse duration to an upper temperature desired value To and, during the no-pulse period, the power supply is controllable to a lower temperature desired value Tu with the alternation between the two desired values being triggered by a pulse generator connected to a desired value input of the control unit.

6 Claims, 1 Drawing Sheet

CIRCUIT ARRANGEMENT FOR DRIVING A PULSE-MODULATED INFRARED-RADIATION SOURCE

FIELD OF THE INVENTION

The invention relates to a circuit arrangement for providing a pulse-modulated power feed to an infrared radiation source having radiation detectable by a receiver.

BACKGROUND OF THE INVENTION

Such pulse-driven infrared-radiation sources are often used to determine the concentrations of components of a gas sample. This is done with the aid of a cuvette arrangement in which the gas sample to be investigated is disposed. The radiation source is connected to a pulse generator driven via a clock. By means of the pulse generator, the voltage supply of the radiation source is switched on and off in correspondence to the pulse clock rate. The infrared-radiation pulses penetrate the measuring cuvette with more or less radiation energy being absorbed in dependence upon the concentration of the gas components to be detected. The radiation energy which is not absorbed reaches an energy chamber in which the useful signal is subjected to a further evaluation. The modulation principle is applied for the reason that the measurement radiation can be clearly distinguished from disturbing fluctuations of the radiation intensity. In this way, a better signal-to-noise ratio is obtained. In this connection, reference may be made to German published patent application DE-OS 30 43 332.

In the known circuit arrangement, the time-dependent course of the measurement signal does not only follow the absorption fluctuations corresponding to the changes in concentration in the measurement cuvette; instead, the time-dependent course of the signal is determined by the heating and cooling characteristic of the radiation source which, in turn, is dependent on the pulse power as well as on the pulse duty factor of the pulse sequences. For this reason, the signal maximum and the signal minimum must be filtered out of an unsymmetrically running signal form with the aid of a complex signal processing method. Furthermore, the radiation sources driven with the known intensity modulation are slow and their radiation intensity is dependent upon the ambient temperature, since the peak temperature and also the heating and cooling time constants are influenced by the heat transfer to the ambient.

SUMMARY OF THE INVENTION

It is an object of the invention to provide a circuit arrangement of the kind described above which is so improved that the radiation source is as independent as possible from its radiation characteristic as well as its thermal characteristics and delivers a rapid and easy to process measurement signal to the receiver uninfluenced by ambient conditions.

The above object is realized in that the energy supply is controlled by means of a control unit during the pulse duration to an upper temperature desired-value To and during the no-pulse period to a lower desired-value Tu with the change between the two desired values being triggered by a pulse generator connected to the desired value input of the control unit.

The advantages of the invention are based substantially on the consideration that after completion of the rise time or decay time of the power feed pulses, stable radiation temperatures are present which are substantially independent of the ambient temperature and the radiator characteristics. The received measurement signal corresponding to the intensity transmitted by the radiator is thereby easy to process and is quickly available after very short transient times.

The energy supply can be so high initially that the temperature pregiven by the upper desired value is reached with a steep rise flank whereafter a reduced power feed is adequate for maintaining the desired value during the control plateau.

Correspondingly, when the radiator is switched off to the lower desired value, the power feed can be first entirely interrupted and, after reaching the lower desired value, can be held at the lower control plateau with only a reduced power feed being necessary.

The radiation source is advantageously arranged as a temperature-dependent resistor in the measuring branch of a bridge circuit with the reference branch of the bridge containing an ancillary resistor which can be switched in by means of a pulse switch. The detecting branch of the bridge circuit is connected to the inputs of an operational amplifier having an output connected in a closed control loop to the radiation source.

By selecting a temperature-dependent resistor as a radiation source, the sensor required for the control loop is formed for inputting the temperature actual value.

The upper power input of the radiator is limited by its temperature-dependent resistance so that the maximum available power can only be fed in at the start of the heat-up time so that a rapid heating time is made possible. A destruction of the radiator by a continuous feed of power which is too high is in this way avoided. The heating power which can be fed in by means of the active resistance control bridge is determined by the selection of the resistors in the reference branch. With the ancillary resistor switched in, the bridge resistance increases at the one input of the operational amplifier so that the voltage difference in the detector branch increases. As a consequence of this imbalance of the bridge circuit, the radiation source is supplied with increased power by means of the operational amplifier until the resistance value of the heated-up radiation source again leads to a bridge balance. In this way, an upper control desired value To is determined for the maximum radiation power of the radiation source.

With the ancillary resistor switched out, the radiation temperature drops so far until a zero balance of the bridge circuit is obtained for a lower control desired value Tu of the radiation heating power. This lower value need not be the ambient temperature; instead, it need only be at a sufficient spacing to the temperature at maximum radiation power so that when cooling, a sufficiently high flank slope of the signal waveform is obtained. The duration for which the ancillary resistance is switched in determines the length of the control plateau. By means of the power tracking of the operational amplifier, a rapid increase from the lower control value Tu to the upper control value To of the radiation temperature is made possible.

To further reduce the rise time when changing from the lower control temperature Tu to the upper control temperature To, the output of the operational amplifier is connected via a transistor switch to the supply voltage necessary for driving the radiation source. In this way, the full power available is applied to the radiator when switching on the transistor so that the stable upper temperature plateau of the radiation intensity is reached in the shortest possible time.

The upper and lower control desired values are adjustable if the resistors for the desired values are configured so as to be adjustable. The pulse switch is configured as a field effect transistor whose source and drain bridge the ancillary resistor. The base of the field effect transistor is then connected to a pulse generator supplying a pulse train which cyclically switches the ancillary resistor in and out so that the radiation source follows correspondingly in its heating power. With a suitable selection of the pulse-to-space ratio, the duration of the stable plateau phases during the lower control temperature Tu and the upper control temperature To can be selected in accordance with requirements.

The advantages of the circuit by means of which the output of the operational amplifier is connected to the supply voltage via the transistor switch can be explained as described below.

During the heat-up phase from the lower control value Tu to the upper control value To, the full operational voltage is applied to the bridge because of the overdriving of the control so that the radiation source reaches its upper control temperature with maximum speed. If this is the case, the control immediately switches back to that bridge voltage which is adequate to maintain the radiator at the upper temperature control value To. The danger of an overheating or destruction of the radiator then no longer exists as is the case for an uncontrolled driving of the radiator with excessive current or voltage pulses. After reaching the upper control value To as well as the lower control value Tu, the radiation power is constant and independent of the ambient temperature so that a very stable infrared-radiation source is realized. Influences from the ambient are compensated in a simple manner. After switching over from the upper control value To to the lower control value Tu, a short flank is obtained with the circuit arrangement described since the bridge current is completely switched off because of the overdriving of the control. After reaching the lower control value Tu, the bridge voltage is then automatically controlled to such a value which is adequate to hold the radiator stable at the lower temperature.

To further evaluate the signal received by the receiver, the receiver is connected via a cascade connected amplifier to a scanning arrangement which scans the received signal in such a manner that a measurement signal So(i) is accepted and processed when reaching the stable condition at the upper control value To and, when reaching the lower control value Tu, a measuring signal Su(i) is accepted and processed. In the particular stable control conditions a series (i) of signals So(i) and Su(i) can be collected, summed and be formed to a modulation measurement value Mw by means of forming the difference of both sums:

$$M_w = 1/n \sum_{i=1}^{n} So(i) - 1/n \sum_{i=1}^{n} Su(i)$$

By rapidly reaching the stable control ranges of the radiation source, it is easily recognizable by means of the scanning arrangement which signals So(i) or Su(i) should be applied for evaluation. It is necessary only to compare the next signal value with the previous one and, when dropping below a pregiven differential threshold, the signal value accepted in this manner can be supplied for processing to a modulation measured value. With this favorable scanning and processing, the influence of the ambient temperature is completely eliminated. This influence remains only in the heat-up flanks and cooling flanks of the signal of the radiation source which, however, can be completely eliminated since the detection of the measured values is now limited only to the stable plateau phases. By repeated detection of the modulation measured values in sequential pulse cycles, a higher quality of the modulation measuring value can be obtained since noise influences of the radiation source and the ambient are further suppressed. An average modulation measured value is then calculable over several measurement cycles (k) which can be obtained as the following:

$$M_{w,k} = 1/k \sum_{m=1}^{k} M_{w,m}$$

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
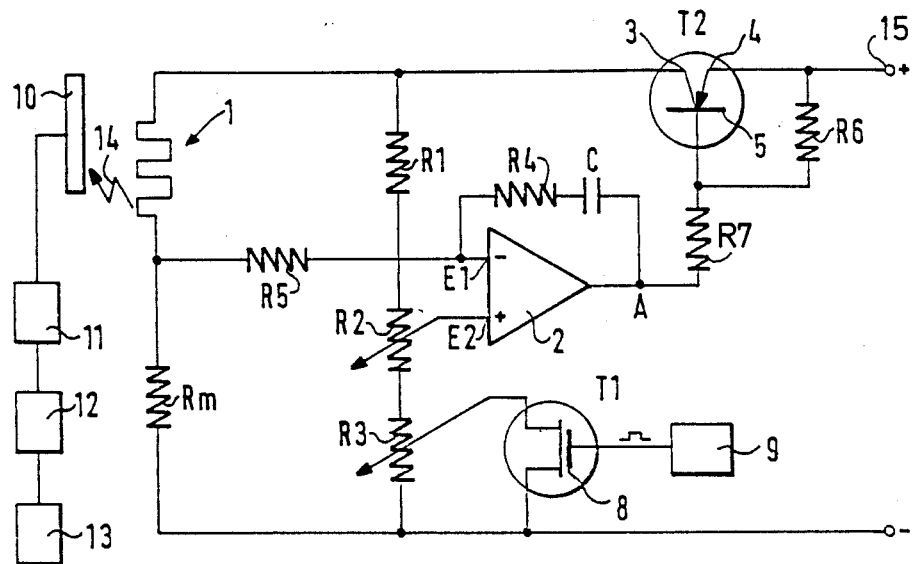
FIG. 1 is schematic of an embodiment of the circuit arrangement according to the invention for pulse driving an infrared-radiation source; and, FIG. 2 is a diagram showing the signal waveform at the receiver.

In FIG. 1, an infrared-radiation source 1 in the form of a temperature-dependent resistor is connected in a bridge circuit and arranged with respect to a measuring resistor Rm in the measuring branch as well as with respect to reference resistor R1 in the reference branch. The reference resistor R1 is connected in series with two series-connected adjustable resistors (R2, R3) also in the reference branch. In the detector branch, the inverting input E1 of an operational amplifier 2 is connected via a series resistor R5 between the radiation source 1 and the measuring resistor Rm. On the other hand, the non-inverting input E2 of the operational amplifier 2 is connected to the adjustable tap of an adjusting resistor R2. The output A and the input E1 of the operational amplifier 2 are interconnected via an RC-component (R4, C). The output A is connected via a base resistor R7 to the base 5 of a transistor switch T2. The collector 3 of the transistor switch T2 is connected to the radiation source 1 and the emitter 4 thereof is connected to the positive voltage supply 15. Emitter 4 and base 5 are coupled via resistor R6.

The adjusting resistor R3 provided in the voltage divider (R2, R3) is connected in parallel to the field effect transistor T1 having a gate 8 connected to a pulse generator 9.

A receiver 10 lies opposite the radiation source 1 and is connected via a preamplifier 11 to a scanning arrangement 12 which, in turn, is connected to an evaluation and display unit 13.

Figure 2:
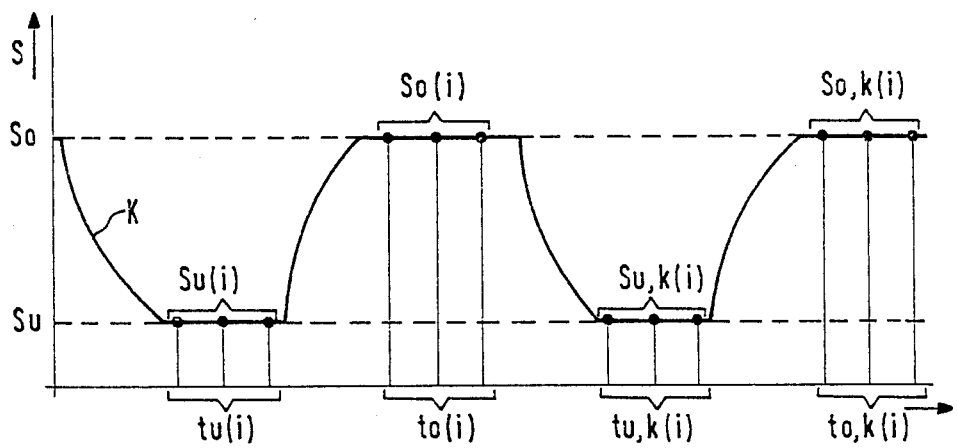

The signals S of the receiver 10 are plotted as a function of time in the diagram of FIG. 2. The course of the curve K shows the signal in dependence upon the radiation power of the radiation source 1 transmitted in a pulse-like manner and is represented in FIG. 1 by the zig-zag arrow 14. A cooling of the radiation source 1 to its lower temperature control value Tu leads to a series of measurement signals Su(i) at the time points tu(i) after reaching the stable lower plateau.

The measurement signals So(i) can be taken off at the receiver 10 after switchover of the heating power for the radiation source 1 for reaching the upper temperature control value To. The signal values Su(i) and So(i) are accepted by the scanning device 12 and supplied to the evaluation unit 13.

In the example according to FIG. 2, three measurement signals Su(i) and So(i) are accepted for each plateau of the lower control temperature Tu and for each plateau of the upper control temperature To. These measurement signals are added in each instance and the sums ar subtracted from each other after being divided by the numeral 3. The result obtained in this manner provides a modulation measuring value for a pulse cycle. This measurement operation can be repeated for further pulse cycles (k) and so on. The more the formation of a modulation value is repeated, the more precise the measurement signal can be differentiated from the disturbing background noise.

It is understood that the foregoing description is that of the preferred embodiments of the invention and that various changes and modifications may be made thereto without departing from the spirit and scope of the invention as defined in the appended claims.

I claim:

1. A circuit arrangement for providing a pulse-modulated power feed to an infrared radiation source which emits radiation detected by a receiver, the circuit arrangement comprising:

power supply means for supplying power for the radiation source;

control means for applying said power to said radiation source to directly control said radiation source alternately between an upper temperature desired value To for the duration of the pulse to cause said radiation source to radiate energy measuring signals to enable said receiver to detect measurement data and a lower temperature desired value Tu during the pulse off-time to cause said radiation source to radiate energy reference signals to enable sand receiver to detect reference data;

said control means having a desired value input; and, pulse generating means connected to said control means at said desired value input for triggering the change between said two desired values (To, Tu).

2. The circuit arrangement of claim 1, said radiation source being a temperature-dependent resistor; and, said control means including:

a bridge circuit having a measuring branch containing said temperature-dependent resistor; said bridge circuit also having a reference branch containing an ancillary resistor and having a detector branch;

an operational amplifier having first and second inputs connected to said detector branch and having an output;

a closed control loop connecting said output and said power supply means to said temperature-dependent resistor;

said second input defining said desired value input; and, said pulse generating means including: switching means for switching said ancillary resistor into and out of said reference branch; and, a pulse generator for driving said switching means and triggering said change between said two desired values (To, Tu).

3. The circuit arrangement of claim 2, said closed control loop including: transistor switching means connected between said output and said power supply means for applying the full power feed of said power supply means directly to said temperature-dependent resistor when said transistor switching means is switched on.

4. The circuit arrangement of claim 3, said switching means for switching said ancillary resistor being a field effect transistor; said field effect transistor having a source and drain bridging said ancillary resistor and having a gate; and, said pulse generator being connected to said gate for driving said field effect transistor.

5. The circuit arrangement of claim 1, said receiver receiving said radiation as a signal waveform S, said arrangement further comprising:

a scanning arrangement connected to said receiver for scanning said signal waveform S and processing the same when a first stable state is reached, to a measuring signal So(i) for the upper pulsed power and, when a second stable state is reached, to a measuring signal Su(i) for the lower pulsed power; and, computing a modulation measurement value $$M_w = 1/n \sum_{i=1}^{n} So(i) - 1/n \sum_{i=1}^{n} Su(i)$$

by forming the weighted difference on (n) added signals So(i) and Su(i).

6. The circuit arrangement of claim 5, comprising an amplifier connected between said receiver and said scanning arrangement.

* * * * *

UNITED STATES PATENT AND TRADEMARK OFFICE
CERTIFICATE OF CORRECTION

PATENT NO. : 4,954,718

DATED : September 4, 1990

INVENTOR(S) : Hans Matthiessen

It is certified that error appears in the above-identified patent and that said Letters Patent is hereby corrected as shown below:

On the title page:
Under item [19] and in item [75], please delete "Mattheissen" and substitute -- Matthiessen -- therefor (two occurrences).

On the title page:
In the Abstract, line 6, please delete "characteristics" and substitute -- characteristic -- therefor.

In column 3, line 55: between "conditions" and "a" add -- , -- therefor.

In column 3, line 57: delete "Mw" and substitute -- $M_w$ -- therefor.

In column 5, line 15: delete "ar" and substitute -- are -- therefor.

In column 5, line 44: delete "sand" and substitute -- said -- therefor.

In column 6, line 45: delete "SO(i)" and substitute -- So(i) -- therefor.

Signed and Sealed this

Seventeenth Day of March, 1992

Attest:

HARRY F. MANBECK, JR.

*Attesting Officer*    *Commissioner of Patents and Trademarks*